(12) United States Patent
Felemban et al.

(10) Patent No.: US 12,216,041 B2
(45) Date of Patent: Feb. 4, 2025

(54) METHOD TO DETECT DIESEL IN FLUID SAMPLES USING PARTIALLY DISSOLVABLE CUVETTES

(71) Applicant: Saudi Arabian Oil Company, Dhahran (SA)

(72) Inventors: Amjad Felemban, Thuwal (SA); Maha Nour, Thuwal (SA); Hamad Al Saiari, Al-Khobar (SA)

(73) Assignee: Saudi Arabian Oil Company, Dhahran (SA)

( * ) Notice: Subject to any disclaimer, the term of this patent is extended or adjusted under 35 U.S.C. 154(b) by 195 days.

(21) Appl. No.: 17/828,912

(22) Filed: May 31, 2022

(65) Prior Publication Data

US 2023/0384210 A1    Nov. 30, 2023

(51) Int. Cl.
*G01N 33/28* (2006.01)
*G01N 21/03* (2006.01)
*G01N 21/3577* (2014.01)

(52) U.S. Cl.
CPC ..... *G01N 21/0303* (2013.01); *G01N 21/3577* (2013.01); *G01N 33/28* (2013.01);
(Continued)

(58) Field of Classification Search
CPC .............. G01N 21/3577; G01N 33/28; G01N 2021/0321; G01N 2021/0389; G01N 21/272
See application file for complete search history.

(56) References Cited

U.S. PATENT DOCUMENTS 3,156,644 A    11/1964  Kunin
4,031,398 A     6/1977  Callis et al.
(Continued)

FOREIGN PATENT DOCUMENTS

CN    210897294 U    6/2020
CN    112349798 A    2/2021
(Continued)

OTHER PUBLICATIONS

Aboaba et al., "Brain tumor quantification equation: Modeled on complete step response algorithm," International Conference on Computer and Communication Engineering (ICCCE 2012), Jul. 3-5, 2012, 988-991, 4 pages.
(Continued)

*Primary Examiner* — Michelle M Iacoletti
*Assistant Examiner* — Maher Yazback
(74) *Attorney, Agent, or Firm* — Fish & Richardson P.C.

(57) ABSTRACT

A method includes providing a cuvette containing a fluid sample having a first substance and emitting light from a light source through the cuvette containing the fluid sample for a duration of time. The cuvette is made of a material that at least partially dissolves in the presence of the first substance. Over the duration of time, the cuvette at least partially dissolves and an intensity of light that passes through the cuvette and the fluid sample changes at a rate. The method also includes receiving, by a light detector, the light that passed through the cuvette, measuring a change in intensity of the received light over the duration of time, and determining that the rate of change in intensity of the light over the duration of time is greater than a threshold rate of change.

20 Claims, 4 Drawing Sheets

(52) U.S. Cl.
CPC ............... *G01N 2021/0321* (2013.01); *G01N 2021/0389* (2013.01)

(56) References Cited

U.S. PATENT DOCUMENTS

| | | | |
|---|---|---|---|
| 4,307,061 | A | 12/1981 | Sarholz |
| 4,651,010 | A | 3/1987 | Javan |
| 5,422,719 | A | 6/1995 | Goldstein |
| 5,818,582 | A | 10/1998 | Fernandez et al. |
| 5,899,567 | A | 5/1999 | Morris, Jr. |
| 5,982,847 | A | 11/1999 | Nelson |
| 6,023,961 | A | 2/2000 | Discenzo |
| 6,507,401 | B1 | 1/2003 | Turner |
| 6,525,325 | B1 | 2/2003 | Andrews et al. |
| 6,692,720 | B1 | 2/2004 | Ninane et al. |
| 6,707,556 | B2 | 3/2004 | Turner |
| 6,911,830 | B2 | 6/2005 | Heremans et al. |
| 7,442,291 | B1 | 10/2008 | Discenzo |
| 7,839,492 | B2 | 11/2010 | Parks, II et al. |
| 8,017,408 | B2 | 9/2011 | Meinhart et al. |
| 8,390,796 | B2 | 3/2013 | Honda |
| 8,408,073 | B2 | 4/2013 | Sparks et al. |
| 8,704,174 | B2 | 4/2014 | Ukon |
| 8,910,514 | B2 | 12/2014 | Sullivan et al. |
| 9,206,386 | B2 | 12/2015 | Tunheim et al. |
| 9,255,875 | B2 | 2/2016 | Denenberg et al. |
| 9,518,918 | B2 | 12/2016 | Mann et al. |
| 9,822,356 | B2 | 11/2017 | Ismagilov et al. |
| 10,060,899 | B2 * | 8/2018 | Hegazi ................. G01J 3/4406 |
| 10,100,966 | B2 | 10/2018 | Vermont et al. |
| 10,317,388 | B2 | 6/2019 | Hegazi et al. |
| 10,502,409 | B2 | 12/2019 | Meinhart et al. |
| 10,643,324 | B2 | 5/2020 | Al Shehri et al. |
| 10,768,094 | B2 | 9/2020 | Amer et al. |
| 10,908,069 | B2 | 2/2021 | Amer et al. |
| 2002/0158211 | A1 | 10/2002 | Gillispie |
| 2003/0133105 | A1 | 7/2003 | Gorelik et al. |
| 2003/0141459 | A1 | 7/2003 | Hegazi et al. |
| 2004/0007675 | A1 | 1/2004 | Gillispie et al. |
| 2004/0124366 | A1 | 7/2004 | Zeng et al. |
| 2006/0114007 | A1 | 6/2006 | Cho |
| 2007/0009423 | A1 | 1/2007 | Handy et al. |
| 2007/0063140 | A1 | 3/2007 | Liu |
| 2007/0095395 | A1 | 5/2007 | Spiess |
| 2007/0187617 | A1 | 8/2007 | Kong |
| 2008/0190354 | A1 * | 8/2008 | Malpas ............... G01N 33/2882 116/206 |
| 2009/0006004 | A1 | 1/2009 | Sens et al. |
| 2009/0216419 | A1 | 8/2009 | Shaw |
| 2010/0269579 | A1 | 10/2010 | Lawrence et al. |
| 2011/0155925 | A1 | 6/2011 | Ukon |
| 2011/0166802 | A1 | 7/2011 | Kong |
| 2011/0236569 | A1 | 9/2011 | Weiller |
| 2011/0267603 | A1 | 11/2011 | Shaw |
| 2011/0303834 | A1 | 12/2011 | Hegazi et al. |
| 2012/0086942 | A1 | 4/2012 | Honda |
| 2013/0333893 | A1 | 12/2013 | Morris |
| 2014/0160540 | A1 * | 6/2014 | Hoshino ............... G02B 5/3016 359/2 |
| 2014/0198313 | A1 | 7/2014 | Tracy et al. |
| 2015/0009495 | A1 | 1/2015 | Li et al. |
| 2015/0085290 | A1 | 3/2015 | Fjerdingstad |
| 2015/0168368 | A1 | 6/2015 | Hegazi et al. |
| 2016/0195509 | A1 | 7/2016 | Jamieson |
| 2016/0202194 | A1 | 7/2016 | Lees |
| 2016/0349198 | A1 | 12/2016 | Barney |
| 2018/0059016 | A1 * | 3/2018 | Battefeld ............... G01N 21/51 |
| 2018/0164263 | A1 * | 6/2018 | Fischer ............... G01N 21/6428 |
| 2019/0257742 | A1 * | 8/2019 | Scheeline ................. G01J 3/18 |
| 2021/0255039 | A1 * | 8/2021 | Morgan, III ............. G01J 3/42 |
| 2022/0136968 | A1 * | 5/2022 | Schwab ............... G01N 1/4055 436/172 |
| 2023/0149921 | A1 | 5/2023 | Nour et al. |
| 2023/0375407 | A1 * | 11/2023 | Muller ............... G01N 21/3103 |
| 2024/0074944 | A1 * | 3/2024 | Weikart ................. C23C 16/50 |

FOREIGN PATENT DOCUMENTS

| | | | |
|---|---|---|---|
| EP | 1496357 A1 * | 1/2005 | ............. G01N 31/22 |
| FR | 2817346 | 5/2002 | |
| WO | WO 2020047469 | 3/2020 | |

OTHER PUBLICATIONS

Al-Abdullah et al., "Flash points and volatility characteristics of gasoline/diesel blends," Fuel, Aug. 2015, 153:67-69, 3 pages.

Al-Samhan et al., "Evaluating scale deposition and scale tendency of effluent water mix with seawater for compatible injection water," Journal of Petroleum Exploration and Production Technology, Jun. 2020, 10(5):2105-2111, 7 pages.

Álvarez et al., "Prediction of Flash-Point Temperature of Alcohol/Biodiesel/Diesel Fuel Blends," Ind. Eng. Chem. Res., Apr. 2019, 58(16):6860-6869, 10 pages.

Beck et al., "Development and characterization of a mobile photoacoustic sensor for on-line soot emission monitoring in diesel exhaust gas," in Analytical and Bioanalytical Chemistry, Apr. 2003, 375(8):1136-1143, 8 pages.

Bedoui et al., "Design and electro-thermal analysis of a platinum micro heater for gas sensors," 13th Int. Multi-Conference Syst. Signals Devices, SSD 2016, 4:558-561, 4 pages.

Bernasconi et al., "Advanced pipeline vibroacoustic monitoring," Pressure Vessels and Piping Conference, Jul. 2013, 5:7, 7 pages.

Bhavani et al., "Diesel to Dual Fuel Conversion Process Development," Artic. Int. J. Eng. Technol., 2018, 7(3):306-310, 5 pages.

Bieler et al., "Calibration of the step response of a 70 GHz sampling oscilloscope using a novel optoelectronic technique," Conference on Precision Electromagnetic Measurements Digest, CPEM Jun. 8-13, 2008, 678-679, 2 pages.

Bridges et al., "Small-signal step response of laser amplifiers and measurement of CO2 laser linewidth," IEEE Journal of Quantum Electronics, Nov. 1968, 4(11): 777-782, 6 pages.

Brueckner et al., "Tunable diode laser absorption spectroscopy as method of choice for non-invasive and automated detection of microbial growth in media fills," Talanta, May 2017, 167:21-29, 9 pages.

Butler et al., "Prediction of Flash Points of Middle Distillates," Ind. Eng. Chem., Apr. 1956, 48(4):808-812, 5 pages.

Chan et al., "Size-controlled growth of CdSe nanocrystals in microfluidic reactors," Nano Lett., Feb. 2003, 3(2):199-201, 3 pages.

Chen et al., "3D-printed microfluidic devices: fabrication, advantages and limitations—a mini review," Analytical Methods, Aug. 2016, 8(31):6005-6012, Aug. 21, 2016, 8 pages.

Demirbas et al., "Diesel Fuel From Waste Lubricating Oil by Pyrolitic Distillation," Pet. Sci. Technol., 33(2): 129-138, Dec. 2015, 12 pages.

Fiorentin et al., "Effect of the finite memory length of a recorder in evaluating its frequency response of from step response," Instrumentation and Measurement Technology Conference, May 21-23, 2002, Proceedings of the 19th IEEE, 1: 787-791, 5 pages.

Foerster et al., "In situ monitoring of microfluidic distillation" Chemical Engineering Journal, 227: 13-21, 2013, 9 pages.

Ghosh et al., "A mass manufacturable thermoplastic based microfluidic droplet generator on cyclic olefin copolymer," Journal of Micromechanics and Microengineering, Apr. 2019, 29(5):055009, 10 pages.

Giordano et al., "Distilling small volumes of crude oil," Fuel, 285: 119072, Feb. 2021, 8 pages.

Gülüm et al., "Density, flash point and heating value variations of corn oil biodiesel-diesel fuel blends," Fuel Process. Technol., Jun. 2015, 134:456-464, 9 pages.

Hafeez et al., "Liquid fuel synthesis in microreactors," React. Chem. Eng., Aug. 2018, 3(4):414-432, 19 pages.

Hartman et al., "Distillation in microchemical systems using capillary forces and segmented flow," Lab Chip, 9(13): 1843-1849, Jul. 2009, 8 pages.

Hartman et al., "Multistep microchemical synthesis enabled by microfluidic distillation," Angew. Chemie—Int. Ed., 49(5): 899-903, Jan. 2010, 5 pages.

(56) References Cited

OTHER PUBLICATIONS

Hibara et al., "Microfluidic distillation utilizing micro-nano combined structure," Chem. Lett., 37(10): 1064-1065, Sep. 2008, 2 pages.

Hua et al., "Determination of sulfur-containing compounds in diesel oils by comprehensive two-dimensional gas chromatography with a sulfur chemiluminescence detector," in Journal of Chromatography A, Nov. 2003, 1019(1-2):101-109, 9 pages.

Jain et al., "Design and Simulation of Microfluidic Passive Mixer With Geometric Variation," International Journal of Research in Engineering and Technology, Feb. 2016, 5(2):55-58, 2016, 5 pages.

Jena et al., "Cyclic olefin copolymer based microfluidic devices for biochip applications: Ultraviolet surface grafting using 2-methacryloyloxyethyl phosphorylcholine," Biomicrofluidics, Mar. 2012, 6(1):012822, 13 pages.

Jena et al., "Micro fabrication of cyclic olefin copolymer (COC) based microfluidic devices," Microsystem Technologies, Feb. 2012, 18(2):159-166, 8 pages.

Jiménez et al., "Chemiluminescence detection systems for the analysis of explosives," J. Hazard. Mater., Jan. 2004, 106(1): 1-8, 8 pages.

Jinno et al., "Identification of polycyclic aromatic hydrocarbons in extracts of diesel particulate matter by supercritical fluid chromatography coupled with an ultraviolet multichannel detector," Analytical Chemistry, 1986, 58(13): 2696-2699, 4 pages.

Kan et al., "Scale Prediction for Oil and Gas Production," SPE Journal, Feb. 2012, 17(2):362-378, 17 pages.

Karnati et al., "Design of Micro-heaters Inspired by Space Filling Fractal Curves," Proc. 2019 IEEE Reg. 10 Symp. TENSYMP 2019, Aug. 2019, 231-236, 6 pages.

Kimmich et al., "Fault detection for modern Diesel engines using signal- and process model-based methods," Control Engineering Practice, Feb. 2005, 13(2):189-203, 15 pages.

Kothare et al., "Microreactors for efficient on-chip fuel processing and hydrogen generation," Nanofabrication: Technologies, Devices, and Applications, Jan. 2005, 5592(19):241, 15 pages.

Kraus et al., "An integrated multiphase flow sensor for microchannels," Exp. Fluids, Jun. 2004, 36(6):819-832, 14 pages.

Lam et al., "Development of multistage distillation in a microfluidic chip," Lab Chip, 11(7):1311-1317, Apr. 2011, 7 pages.

Lam et al., "Towards an understanding of the effects of operating conditions on separation by microfluidic distillation," Chem. Eng. Sci., 66(10): 2098-2106, May 2011, 9 pages.

Lamonte et al., "Cyclic Olefin Copolymers," Advanced Materials & Processes, Mar. 2001, 159(3):33-36, 4 pages.

Li et al., "Isoelectric focusing in cyclic olefin copolymer microfluidic channels coated by polyacrylamide using a UV photografting method," Electrophoresis, Apr. 2005, 26(9):1800-1806, 7 pages.

Lin et al., "Integrated microfluidic reactors," Nano Today, Dec. 2009, 4(6):470-481, 12 pages.

Liu et al., "Micro-distillation system for formaldehyde concentration detection," Chem. Eng. J., 304: 419-425, Nov. 2016, 7 pages.

Ljubas et al., "Influence of engine oils dilution by fuels on their viscosity, flash point and fire point," NAFTA, 2010, 61(2):73-79, 7 pages.

McGann et al., "Lean fuel detection with nanosecond-gated laser-induced breakdown spectroscopy," Combustion and Flame, Feb. 2021, 224:209-218, 10 pages.

McGuire et al., "Detection of the aromatic molecule benzonitrile (c-C6H5CN) in the interstellar medium," Science, Jan. 2018, 359(6372):202-205, 5 pages.

Mehra et al., "Six-wafer combustion system for a silicon micro gas turbine engine," J. Microelectromechanical Syst., Dec. 2000, 9(4):517-527, 11 pages.

Mendonca et al., "Application of step response impedance spectroscopy for detection of skin irritation," Engineering in Medicine and Biology Society, Sep. 17-21, 2003; Proceedings of the 25th Annual International Conference of the IEEE, 4: 3215-3217, 3 pages.

mitsuichemicals.com [online], "APEL," 2020, retrieved on Feb. 14, 2022, retrieved from URL <https://jp.mitsuichemicals.com/en/special/apel/about/properties/>, 7 pages.

Mulrooney et al., "Detection of carbon dioxide emissions from a diesel engine using a mid-infrared optical fibre based sensor," Sensors Actuators, A Phys., May 2007, 136(1):104-110, 7 pages.

Nunes et al., "Cyclic olefin polymers: Emerging materials for lab-on-a-chip applications," Microfluidics and Nanofluidics, Apr. 2010, 9(2-3):145-161, 17 pages.

Olajire, "A review of oilfield scale management technology for oil and gas production," Journal of Petroleum Science and Engineering, Nov. 2015, 135:723-737, 45 pages.

Petermann, "Chapter 4: Intensity-Modulation Characteristics of Laser Diodes," Laser diode modulation and Noise, Kluwer Academic, 1991, 78-118, 41 pages.

Rowland et al., "The Automated Assessment of Ultrasound Scanner Lateral and Slice Thickness Resolution: Use of the Step Response," Ultrasound in Medicine & Biology, 35(9): 1525-1534, Sep. 2009, 10 pages.

Schuresko et al., "Carboxylation kinetics of hemoglobin and myoglobin: linear transient response to step perturbation by laser photolysis," Biophysical Journal, 24(1): 382-383, Oct. 1978, 2 pages.

Seo et al., "Continuous microfluidic reactors for polymer particles," Langmuir, Dec. 2005, 21(25):11614-11622, 9 pages.

Soud, "Downstream oil theft: countermeasures and good practices," Atlantic Council, May 2020, retrieved on Feb. 16, 2022, retrieved from URL <https://www.atlanticcouncil.org/wp-content/uploads/2020/05/AC_OilTheft-Final-1.pdf>, 56 pages.

Spannhake et al., "High-temperature MEMS heater platforms: Long-term performance of metal and semiconductor heater materials," Sensors, Apr. 2006, 6(4):405-419, 15 pages.

Sumitomo Heavy Industries Process Equipment Co., Ltd., "Consider a mixing vessel as a huge viscometer." Accessed: Aug. 20, 2020. [Online]. Available: https://www.shi-pe.shi.co.jp/english/technology/mixing-lecture/004/index.html, 3 pages.

Taghizadeh-Alisaraei et al., "Fault detection of injectors in diesel engines using vibration time-frequency analysis," Applied Acoustics, Jan. 2019, 143:48-48, 11 pages.

thomassci.com [online], "Multi-Position Hot Plate Stirrer," 2022, retrieved Feb. 15, 2022, retrieved from URL <https://www.thomassci.com/Equipment/Hot-Plates/_/Multi-Position-Hot-Plate-Stirrer?q=Multi%20Position%20Hotplate%20Stirrer>, 2 pages.

Udonne, "A comparative study of recycling of used lubrication Oils using distillation, acid and activated charcoal with clay methods," J. Pet. Gas Eng., Feb. 2011, 2(2):12-19, 8 pages.

Vahdati et al., "External corrosion detection of oil pipelines using fiber optics." Sensors 20.3, 684, Jan. 2020, 16 pages.

Van-Den-Begin et al., "Fast adsorption-desorption kinetics of hydrocarbons in silicalite-1 by the single-step frequency response method," Zeolites, 9(4): 287-292, Jul. 1989, 6 pages.

Wardzinska et al., "Step response sensitivity of VLSI interconnects," 17th IEEE Workshop on Signal and Power Integrity (SPI), May 12-15, 2013, 4 pages.

Wronski et al., "The step response: a method to characterize mechanisms of renal blood flow autoregulation," American Journal of Physiology—Renal Physiology, Sep. 3, 2003, 285(4): F758-764, 7 pages.

Yamagata et al., "Synthesis of highly fluorescent diketopyrrolopyrrole derivative and two-step response of fluorescence to acid," Tetrahedron Letters, Mar. 24, 2010, 51(12): 1596-1599, 4 pages.

Yang et al., "Determination of sulfur compounds in catalytic diesel oil by gas chromatography with atomic emission detector and its applications," Se Pu, Nov. 2002, Abstract, 2 pages.

Youn et al., "Fabrication of micro mold for hot-embossing of polyimide microfluidic platform by using electron beam lithography combined with inductively coupled plasma," Microelectron. Eng., 2008, 85( 5-6):918-921, 4 pages.

Yu et al., "A novel polyimide based micro heater with high temperature uniformity," Sensors Actuators, A Phys., Feb. 2017, 257:58-64, 7 pages.

Zhang et al., "Spray model based on step response theory," Fuel, May 2012, 95(1): 499-503, 5 pages.

(56) References Cited

OTHER PUBLICATIONS

Zhang et al., "Design of the microfluidic chip of oil detection," Applied Mechanics and Materials, 117-119: 517-520, 2012, 5 pages.

Zhao et al., "Design principles and fabrication method for a miniaturized fuel gas combustion reactor," Sensors, The 3rd Conference on MicroFluidic Handling Systems, Oct. 2017, 4 pages.

SAIP Examination Report in Saudi Arabian Appln. No. 123447144, dated Oct. 20, 2024, 12 pages with English translation.

\* cited by examiner

METHOD TO DETECT DIESEL IN FLUID SAMPLES USING PARTIALLY DISSOLVABLE CUVETTES

TECHNICAL FIELD

This disclosure relates to systems and methods for detecting diesel in hydrocarbon mixtures.

BACKGROUND

Countermeasures are used to actively combat criminal exploitation and illegal diesel smuggling practices. One countermeasure is fuel marking. Molecular fuel markers are continuously added to hydrocarbon mixtures over the entire fuel production. The markers are detected using complex measuring instruments, such as gas chromatography or X-ray fluorescence (XRF) spectrometers capable of detecting diesel in low concentrations. Other counter exploitation technologies include digitized metering, GPS tracking, aerial surveillance, and various monitoring platforms.

SUMMARY

In certain aspects, a method is disclosed for detecting a level of a substance in a fluid sample. The method includes providing a cuvette containing a fluid sample having a first substance. The cuvette includes a material that is configured to at least partially dissolve in the presence of the first substance. The method also includes emitting light from a light source through the cuvette containing the fluid sample for a duration of time. The cuvette at least partially dissolves over the duration of time such that an intensity of light that passes through the cuvette and the fluid sample changes at a rate over the duration of time. The method includes receiving, by a light detector of the system, the light that passed through the cuvette and the fluid sample and measuring a change in intensity of the received light over the duration of time. The method also includes determining that the rate of change in intensity of the light over the duration of time is greater than a threshold rate of change and outputting, in response to the determination, a signal indicating that the fluid sample includes the first substance.

In some methods, the first substance is an aromatic compound, for example, diesel, gasoline, or lubrication oils.

Some fluid samples are a refined petroleum product.

In some embodiments, the material of the cuvette is cyclic olefin polymer (COP). Some materials are first materials and the cuvette also includes a second material that is different from the first material. The cuvette can include sidewalls having a first layer defining a cavity and a second layer. The sample fluid may be disposed in the cavity and the first layer may include COP and the second layer includes the second material. The first layer can be arranged between the cavity and the second layer. The second material may be glass or quartz.

In some methods, the threshold rate of change is zero.

In some methods, the threshold rate of change is greater than zero.

In some embodiments, the method includes determining a level of a first substance in the fluid sample based on the rate of change in intensity of the light over the duration of time. The rate of change in intensity of the light over the duration of time may be proportional to the level of the first substance in the fluid sample.

In certain aspects, detecting a level of diesel in a fluid sample includes emitting, from a light source of a system, light through a cyclic olefin polymer (COP) cuvette containing the fluid sample. The COP of the cuvette is at least partially dissolvable by diesel. The method also includes receiving, by a light detector of the system, the light and measuring the intensity of the detected light over a duration of time. The method also includes determining, by a computer sub-system of the system, a level of diesel in the fluid sample based on the measured intensity of the detected light over the duration of time.

In some methods, determining a level of the diesel in the fluid sample based on the calculated intensity over the duration of time includes calculating a rate of change of the intensity of the detected light over the duration of time.

In some embodiments, determining the level of the diesel in the fluid sample based on the calculated intensity over the duration of time includes determining a presence of the diesel based on the calculated intensity of the detected light over the duration of time.

In some methods, determining the presence of the diesel based on the calculated intensity of the set of detected light over the duration of time includes calculating a measured rate of change of the intensity of the detected light over the duration of time. A positive measured rate of change may indicate the presence of the diesel. A zero or negative measured rate of change may indicate the absence of the diesel.

The details of one or more embodiments are set forth in the accompanying drawings and the description below. Other features, objects, and advantages will be apparent from the description and drawings, and from the claims.

DESCRIPTION OF DRAWINGS

Like reference symbols in the various drawings indicate like elements.

DETAILED DESCRIPTION

A system is disclosed for detecting a first substance in a fluid sample. The system detects the presence of the first substance and/or detects a level of the first substance in the fluid sample. The fluid sample can be taken from a larger volume of a hydrocarbon mixture and the first substance can be diesel. The system includes a container made of a material dissolvable by the first substance, a light source, and a light detector. In use, the sample is held in the container and, if the first substance is present, the container begins to dissolve. The light beam sends a continuous beam or set of beams through the container and the light is received by the light detector. The intensity of the light increases as the material of the container dissolves. The light is received by the detector and the intensity of detected light is plotted over time. A computer sub-system of the system can calculate a trend line having a slope. If the intensity of detected light increases over time (e.g. has a positive slope), the system can confirm that the first substance is present. If the intensity of detected light does not increase over time (e.g. has a zero slope), the system can confirm that the first substance is absent. In some cases, the system can determine if a predetermined amount of the first substance is present by calculating the slope of the trend line.

The disclosed systems and methods are capable of detecting a first substance, for example diesel, in a mixture without the use of additives or markers, resulting in a simpler less expensive detection system. Further, the system can be used in the field or on site which can result in quicker intervention against diesel smuggling and can prevent customers from buying a diluted product.

Figure 1:
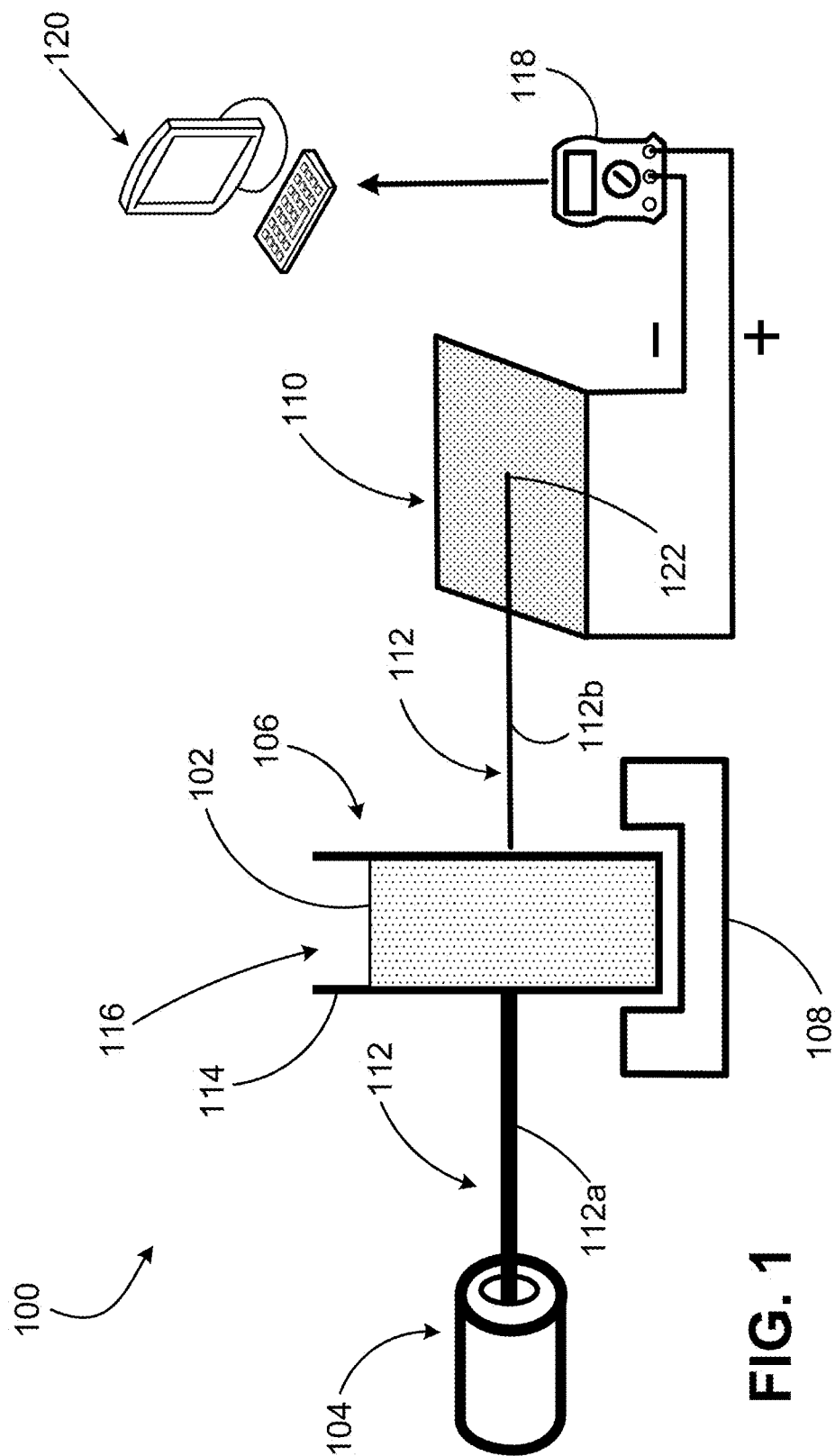
FIG. 1 is a view of a system for detecting a first substance in a fluid sample.

FIG. 1 is a view of a system 100 for detecting a first substance in a fluid sample 102. The system 100 includes a light source 104, a cuvette 106 arranged in a cuvette holder 108, and a light detector 110. The cuvette 106 and cuvette holder 108 are arranged between the light source 104 (e.g., a laser) and the light detector 110 so that light 112 generated by the light source 104 passes through the cuvette 106. The light detector 110 is configured to receive light 112 continuously over a duration of time. In some cases, the light detector is configured to receive a set of light beams flashed or emitted over uniform or non-uniform intervals. Some emitted lights are a single collimated beam of light or variations thereof. The fluid sample may be a sample from a refined petroleum product (e.g., a hydrocarbon mixture) and the first substance may be an aromatic compound (e.g., diesel, lubrication oils, or gasoline).

The cuvette 106 is transparent such that the light 112 generated by the light source 104 passes through walls 114 of the cuvette 106. The walls 114 of the cuvette 106 form a cavity 116 for receiving the fluid sample 102. The cuvette 106 is made of a material dissolvable by the first substance in the fluid sample 102. For example, the cuvette is made of cyclic olefin polymer (COP) and the first substance is an aromatic compound (e.g., diesel, gasoline, lubrication oils, or toluene). The light 112 includes a portion of emitted light 112a that has not passed the cuvette 106 and a portion of received light 112b that has passed the cuvette 106. The cuvette 106 lessens the intensity of the emitted light 112a as compared to the received light 112b. If the first substance dissolves a portion of the cuvette wall 114, the transparency of the cuvette 106 increases. Some cuvettes are at least partially transparent or opaque.

In some cases, the walls of the cuvette are formed by different materials, for example a non-dissolvable transparent material with a dissolvable insert (e.g., a lining, section, strip, portion, area, or layer formed by the dissolvable material). Non-dissolvable materials includes glass and quartz. Some cuvettes have a first inner layer defining the cavity. The first layer may be made of COP or another material dissolvable by the first substance. The cuvette can also include a second layer, externally surrounding the first layer. The second layer can be made of a second material, for example a non-dissolvable material. In use, the fluid sample is disposed in the cavity of the first layer of the cuvette.

The system 100 also includes a signal intensity measurement tool, for example, a multimeter 118, and a computer sub-system 120 for processing and analyzing signals generated by the multimeter 118 and/or light detector 110. The computer sub-system 120 is connected by wire or wirelessly to the light source 104, the light detector 110, and the multimeter 118. In some cases, the computer sub-system is only connected to the multimeter. The light detector 110 provides a detector signal which can to be processed by the multimeter 118 to convert the detector signal into a measured light intensity. Some light detectors automatically convert light intensity into a digital signal and provide that as output to the computer sub-system. In such systems, the multimeter may be omitted. The light detector 110 includes a detection surface 122 that receives the light 112.

The computer sub-system 120 is operable to receive signals from the multimeter 118 and/or the light detector 110 and calculate the measured light intensity of the light 112b detected by the light detector 110. The computer sub-system 120 is operable to wirelessly connect to other computer sub-systems (e.g., laptops, computers, portable phones, smart phones, tablets, smart devices) to transmit or receive data. The computer sub-system 120 is also operable to generate an output signal that notifies or alerts the operator of the presence of the first substance. Some computer sub-systems are operable to generate an output signal that notifies or alerts the operator that a level or amount of the first substance is present in the fluid sample. The computer sub-system can also alert or notify the operator that an absence of the first substance is detected. The computer sub-system can include a controller operable to control the computer sub-system, the light source, the light detector, and the multimeter.

The system may be in the form of a lab system mounted on a lab bench. In some embodiments, the system is a portable hand held system. In some cases, the light source, cuvette, cuvette holder, and light detector are arranged in a portable housing and the computer sub-system is wirelessly connected to the light detector or to a controller of the portable housing. The controller may be operable to control the light source and light detector.

Figure 2:
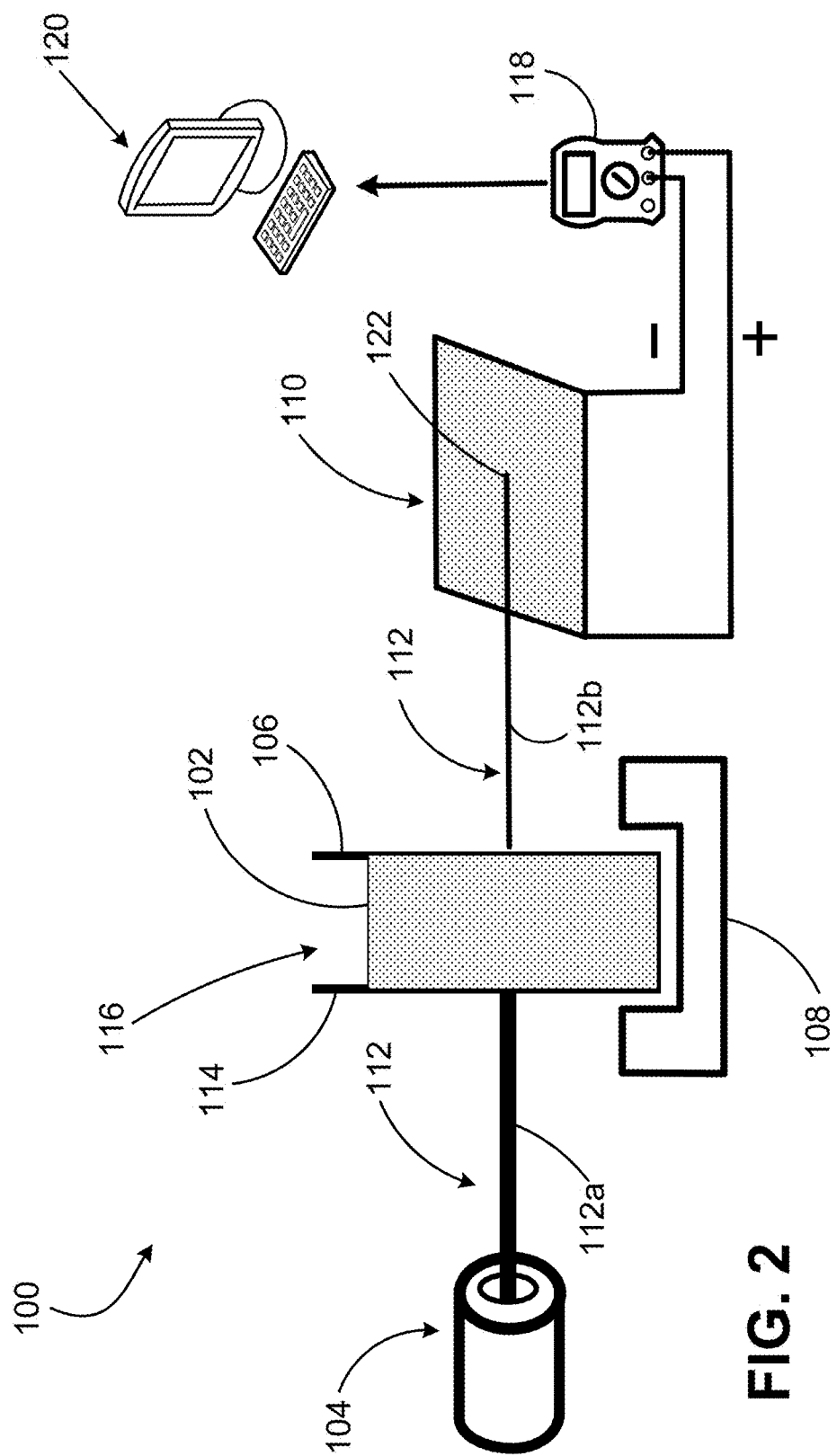
FIG. 2 is a view of the system for detecting the first substance in the fluid sample, after a duration of time has expired.

FIG. 2 is a view of the system 100 for detecting the first substance in the fluid sample 102, after a duration of time has expired. The fluid sample 102 containing a first substance (e.g., an aromatic compound or diesel) has partially dissolved the material of the cuvette 106, reducing the thickness of the walls 114 of the cuvette 106 and increasing the intensity of light 112b detected by the light detector 110. The predetermined amount of time (e.g., duration of time) is about 5 minutes to about 2 hours. In some cases, the duration of time is about 5 minutes to about 3 hours, e.g., about 15 minutes to about 40 minutes about 20 minutes to about 45 minutes, about 10 minutes to about 1 hour, e.g., about 30 minutes to about 2 hours.

Figure 3:
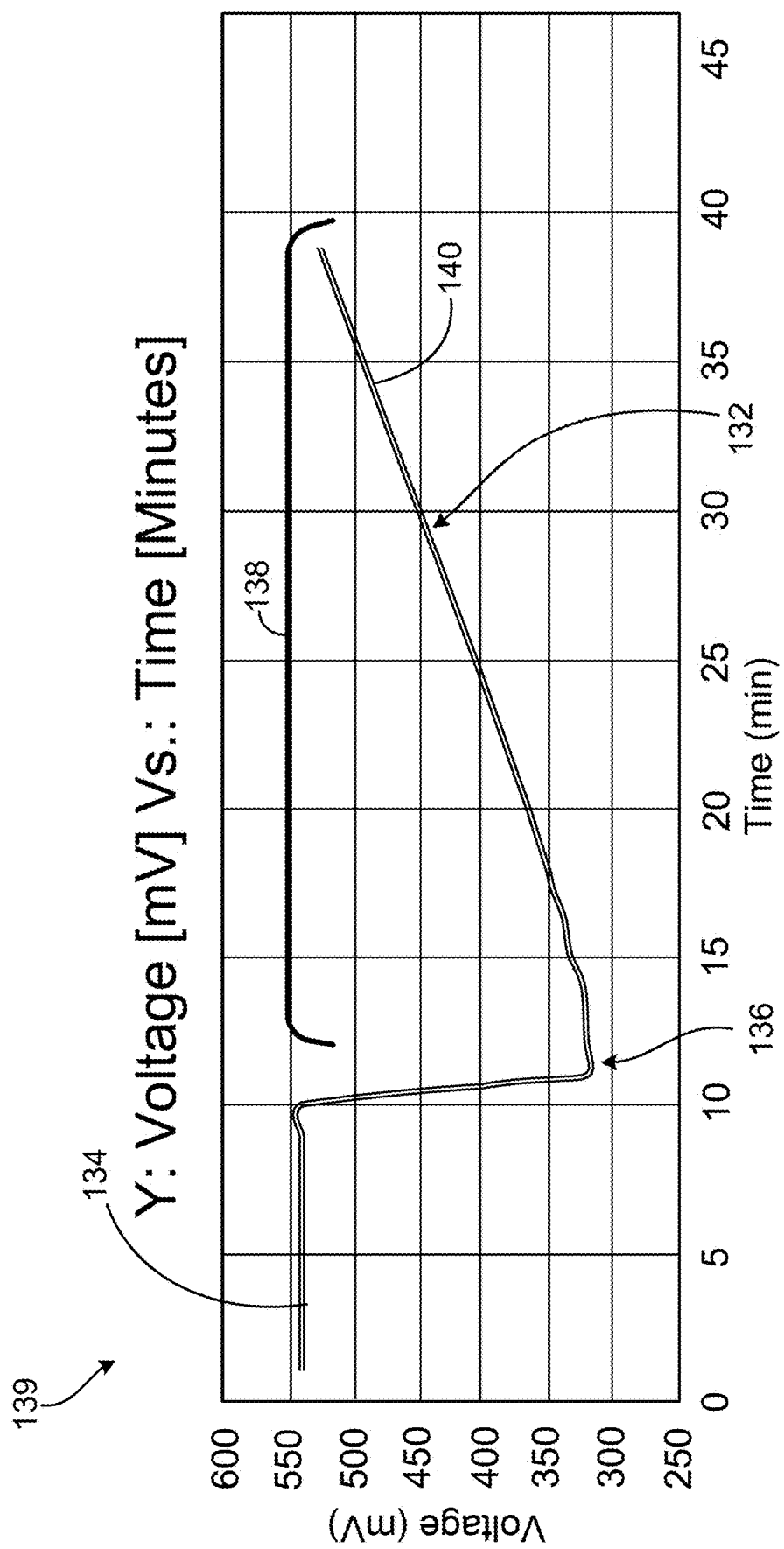
FIG. 3 is a graph of plotted intensity data generated by a light detector of the system.

FIG. 3 is a graph 139 of plotted intensity data 132 generated by a light detector 110 (FIG. 1) of the system 100 (FIG. 1). The graph 139 and data 132 are representative of a fluid sample containing the first substance. The intensity data 132 begins with a first plateau 134 prior to the cuvette 106 being loaded or inserted into the cuvette holder 108. The measured intensity then is maintained or drops slightly as the cuvette 106 is inserted into the cuvette holder 108 due to the light passing through the walls 114 of the cuvette 106. The intensity data 132 has a sharp drop due to the operator loading the fluid sample 102 in the cavity 116 of the cuvette 106. Then the intensity data 132 shows a second plateau 136 where the intensity measurements stabilize. The intensity data 132 enters a detection portion 138. The detection portion 138 begins after the fluid sample 102 is loaded into the cuvette 106 and extends a predetermined amount of time (e.g., a duration of time). There may be a delay of about 1 second to about 5 minutes after insertion of the fluid sample before the detection portion begins to allow the measurements to stabilize and/or the fluid to settle. The computer sub-system 120 is operable to determine the presence of the first substance in the fluid sample 102 by analyzing the detection portion 138 of the intensity data 132 over the duration of time.

In the detection portion 138, the intensity data 132 exhibits a linear increase 140 (e.g., a positive rate of change over the duration of time) as the first substance (e.g., diesel) in the fluid sample 102 dissolves the material of the cuvette 106 (e.g., COP). The computer sub-system 120 generates a linear trend line and/or determines average rate of change of the intensity data 132 in the detection portion 138. In some cases, the average rate of change is the slope of the linear trend line. If the (average) rate of change of the intensity data in the detection portion is greater than a threshold rate of change, the computer sub-system 120 confirms that the fluid sample 102 contains the first substance (e.g., diesel). If the (average) rate of change of the intensity data in the detection portion is equal to or less than a threshold rate of change the computer sub-system 120 confirms that the first substance is absent in fluid sample 102. When determining the presence of the first substance, the threshold rate of change is zero. As such, a positive rate of change of the intensity data 132 in the detection portion 138 would indicate a presence of the first substance in the fluid sample 102. In some systems, the threshold rate of change can be greater than zero or less than zero. The rate of change (e.g., the slope of a linear trend line of the detection section) is an indication of the concentration and amount of the substance in the fluid sample. The higher the concentration, the faster the rate of dissolution of the walls and the more rapid increase in intensity.

Figure 4:
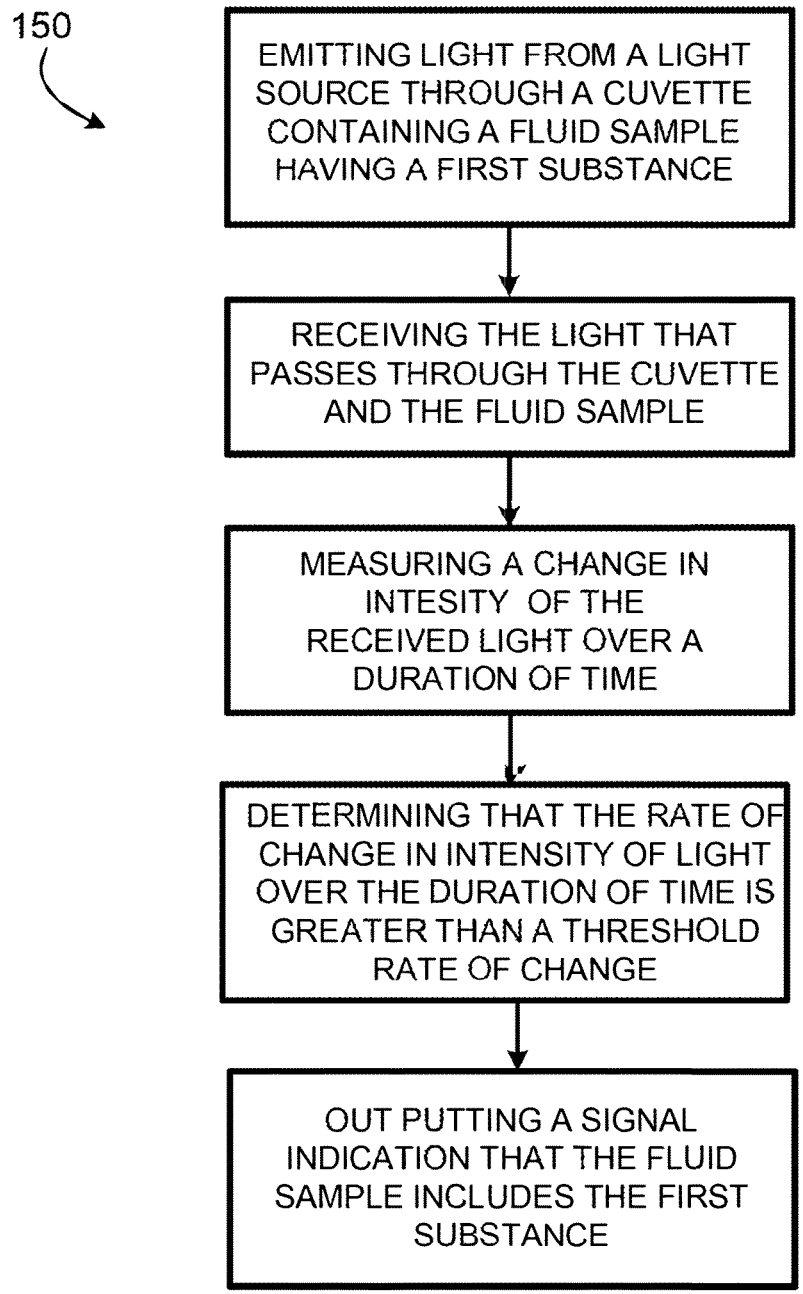
FIG. 4 is a flowchart of a method for operating the system.

FIG. 4 is a flowchart of a method 150 for operating a detection system. The method 150 is described with reference to the detection system 100, however, the method 150 can also be used with other detection systems. The method 150 is used to determine the presence of a first substance in a fluid sample. For example, the fluid sample may be a hydrocarbon mixture, the first substance may be diesel, and the material of the cuvette may be COP. The method can also be used to determine a level, amount, or concentration of the first substance in the fluid sample.

The method 150 includes providing the system 100 on a lab bench, as an in-field device, or as a portable device. The system 100 includes the cuvette 106 for holding a fluid sample 102, the cuvette holder 108 for receiving the cuvette 106, the light source 104 (e.g., a laser), a light detector 110 (e.g., a light receiver or a photo detector), a multimeter 118, and a computer sub-system 120. The cuvette 106 is made of a material (e.g., COP) that is configured to at least partially dissolve in the presence of the first substance. In some cases, the cuvette is formed by a first dissolvable material and a second non-dissolvable material.

The light source 104 is activated so that the light 112 intersects the light detector 110 on the detection surface 122. The cuvette 106 is inserted into the cuvette holder 108 and the fluid sample 102 is loaded into the cavity 116 of the cuvette holder 108. In some cases, the cuvette with the fluid sample is inserted into the cuvette holder. The light source 104 emits continuous light 112 through the cuvette 106 containing the fluid sample 102 for a duration of time. Some light sources emit a set of light beams at uniform or non-uniform intervals. If the first substance is present in the fluid sample, the cuvette at least partially dissolves over the duration of time. As the cuvette 106 dissolves, the intensity of the light 112 that passes through the cuvette 106 and the fluid sample 102 changes over the duration of time. In some systems, the first substance is diesel and the material of the cuvette is COP. In such a case, the diesel dissolves the COP but does not change the color or transparency of the fluid sample. As such, any measured increase in intensity of the light occurs due to the dissolution of the walls of the cuvette. In some systems, the dissolution of the material of the cuvette alters the transparency of the fluid sample. In such a case, any measured decrease in intensity of the light occurs due to the dissolution of the cuvette into the fluid sample.

The method 150 also includes receiving, by the light detector 110 of the system 100, the light 112*b* that passed through the cuvette 106 and the fluid sample 102. The light detector 110 generates received light signals and transmits the received light signals to the multimeter 118. The multimeter 118 coverts the received light data into measured intensity data and transmits the measured intensity data to the computer sub-system 120. The measured intensity data contains the measured intensity of the received light 112 over the duration of time. The duration of time starts after the fluid sample 102 is loaded into the cuvette 106. In some cases, the duration of time starts after the cuvette containing the fluid sample is inserted into the cuvette holder.

The computer sub-system 120 then measures or calculates a rate of change in intensity of the received light 112*b* over the duration of time. The measured or average rate of change may be calculated by generating a linear trend line of the intensity data over the duration of time. The slope of the trend line is the measured (or average) rate of change. The average rate of change may also be calculated by averaging the difference between each intensity measurement of the intensity data. In some cases, the rate of change is calculated by averaging a rolling window averaging over time (e.g., over the duration of time). In the method 150, the first substance (e.g., diesel) is present in the fluid sample 102. As such, the measured intensity data generated by the multimeter 118 and transmitted to the computer sub-system 120 is similar to the intensity data 132, described with reference to FIG. 3. The measured intensity data has a detection portion over the duration of time with a linear increase (e.g., positive rate of change). The computer sub-system 120 generates a linear trend line of the detection portion of the measured intensity data and determines measured rate of change by the slope of the linear trend line.

The computer sub-system 120 compares the measured (positive) rate of change to a threshold rate of change. The threshold rate of change is known. In the system 100 that tests for the presence of the first substance in the fluid sample 102, the threshold rate of change is zero. If the computer sub-system 120 determines that the measured rate of change is greater than the threshold rate of change, the computer sub-system 120 outputs a signal indicating that the fluid sample 102 includes the first substance. If the computer sub-system 120 determines that the measured rate of change is less than or equal to the threshold rate of change, the computer sub-system outputs a signal indicating that the first substance is absent in the fluid sample 102.

The signal from the computer sub-system may be a visual, auditory, and/or tactical alert, notification, or message. In some cases, the signal may be a set of color lights, one color indicating that the first substance is present and another color indicating that the first substance is absent. Some computer sub-systems include transceivers configured to send data or notifications to a separate computer system. For example, the computer sub-system can notify the operator by a visual notification on a screen and transmit to another computer that the system detected or did not detect the first substance in a fluid sample.

In some cases, the system tests for a known level of the first substance, not only the presence of the substance. In such a system, the threshold rate of change may be greater than zero, for example a threshold rate of change that corresponds to a diesel level of about 0.1%, a threshold rate of change that corresponds to a diesel level of about 0.25%, a threshold rate of change that corresponds to a diesel level of about 0.5%, a threshold rate of change that corresponds to a diesel level of about 1%, a threshold rate of change that corresponds to a diesel level of about 1.5%, a threshold rate of change that corresponds to a diesel level of about 2%, a threshold rate of change that corresponds to a diesel level of about 2.5%, a threshold rate of change that corresponds to a diesel level of about 3%, a threshold rate of change that corresponds to a diesel level of about 3.5%, a threshold rate of change that corresponds to a diesel level of about 4%, a threshold rate of change that corresponds to a diesel level of about 4.5%, a threshold rate of change that corresponds to a diesel level of about 5%, a threshold rate of change that corresponds to a diesel level of about 7%, a threshold rate of change that corresponds to a diesel level of about 10%, a threshold rate of change that corresponds to a diesel level of about 15%, a threshold rate of change that corresponds to a diesel level of about 20%, or a threshold rate of change that corresponds to a diesel level of about 25%. The level of diesel may be calculated on the computer system, based on the slope or rate of change of the intensity data in the detection portion.

In this method, the computer sub-system calculates a rate of change in intensity of the received light over the duration of time. The measured or average rate of change may be calculated by generating a linear trend line of the intensity data over the duration of time. The slope of the trend line is the measured (or average rate of change). The average rate of change may also be calculated by averaging the difference between each intensity measurement of the intensity data. The method may have a threshold rate of change that is greater than zero. The non-zero rate of change corresponds to a predetermined amount (e.g., a level or concentration) of the first substance. As such, if the measured rate of change is greater than or equal to the non-zero threshold rate of change, the computer sub-system confirms that the first substance is present in the fluid sample at or greater than the known amount of the first substance. The computer sub-system can output a signal indicating that the fluid sample includes the first substance and/or that the fluid sample includes the first substance at or above the predetermined amount (e.g., 0.5% diesel). If the computer sub-system determines that the measured rate of change is less than the non-zero threshold rate of change, the computer sub-system can output a signal indicating that the first substance is absent in the fluid sample and/or that the first substance is not present at the predetermined amount (e.g., 0.5% diesel).

In some cases, the system can test for a known level of the first substance when the dissolution of the material decreases the transparency of the fluid sample. In such a case the threshold rate of change may be less than zero, for example a threshold rate of change that corresponds to a first substance level of about 0.1%, a threshold rate of change that corresponds to a first substance level of about 0.25%, a threshold rate of change that corresponds to a first substance level of about 0.5%, a threshold rate of change that corresponds to a first substance level of about 1%, a threshold rate of change that corresponds to a first substance level of about 1.5%, a threshold rate of change that corresponds to a first substance level of about 2%, a threshold rate of change that corresponds to a first substance level of about 2.5%, a threshold rate of change that corresponds to a first substance level of about 3%, a threshold rate of change that corresponds to a first substance level of about 3.5%, a threshold rate of change that corresponds to a first substance level of about 4%, a threshold rate of change that corresponds to a first substance level of about 4.5%, a threshold rate of change that corresponds to a first substance level of about 5%, a threshold rate of change that corresponds to a first substance level of about 7%, a threshold rate of change that corresponds to a first substance level of about 10%, a threshold rate of change that corresponds to a first substance level of about 15%, a threshold rate of change that corresponds to a first substance level of about 20%, a threshold rate of change that corresponds to a first substance level of about 25%, a threshold rate of change that corresponds to a first substance level of about 30%, a threshold rate of change that corresponds to a first substance level of about 40%, a threshold rate of change that corresponds to a first substance level of about 50%, a threshold rate of change that corresponds to a first substance level of about 60%, a threshold rate of change that corresponds to a first substance level of about 70%, a threshold rate of change that corresponds to a first substance level of about 45%, a threshold rate of change that corresponds to a first substance level of about 80%, a threshold rate of change that corresponds to a first substance level of about 90%, or a threshold rate of change that corresponds to a first substance level of about 100%.

The measured rate of change of the intensity of detected light over the duration of time is proportional to the amount of the first substance in the fluid sample. In some systems, the computer sub-system is configured to calculate or determine the level of the first substance present in the fluid sample. For example, the computer sub-system may calculate the amount of the first substance in the fluid sample based on the rate of change of the intensity of detected light.

While the detection portion of the intensity data has been described as having a linear increase, some detection portions have a linear decrease (e.g., a negative slope), a zero slope, or an exponential shape.

While the systems and methods have been described with the first substance being an aromatic compound or diesel and the cuvette material being COP, some system test for a first substance of other aromatic chain compounds. Some cuvettes are made of any material dissolvable by aromatic chain compound.

While the threshold rate of change has been described as a single threshold, some methods include multiple threshold rates of changes to detect both the presence of a first substance and a known level of the first substance. For example, the system may implement the method 150 to detect a presence of the first substance. When testing the presence of the first substance, the computer-sub system applies a first threshold rate of change (e.g., zero). If the measured rate of change of the intensity of the received light is greater than the first threshold rate of change, the computer sub-system may continue to apply a second threshold rate of change that corresponds to a known amount (level or concentration) of the first substance. For example, the first threshold may correspond to a concentration of 0% diesel and the second threshold may correspond to a concentration of 0.5% diesel. This configuration can increase downstream testing, for example confirming at gas stations that the gas product has the correct level of gas and has not been diluted.

A number of embodiments have been described. Nevertheless, it will be understood that various modifications may be made without departing from the spirit and scope. Accordingly, other embodiments are within the scope of the following claims.

What is claimed is:
1. A method for detecting a level of a substance in a fluid sample, the method comprising:

providing a cuvette containing a fluid sample having a first substance, the cuvette comprising a material that is configured to at least partially dissolve in the presence of the first substance;

emitting light from a light source through the cuvette containing the fluid sample for a duration of time, wherein the cuvette at least partially dissolves over the duration of time such that an intensity of light that passes through the cuvette and the fluid sample changes at a rate over the duration of time;

receiving, by a light detector of the system, the light that passed through the cuvette and the fluid sample;

measuring a change in intensity of the received light over the duration of time;

determining if the rate of change in intensity of the light over the duration of time is greater than a threshold rate of change; and outputting, in response to the determination, a signal indicating that the fluid sample includes the first substance.

2. The method according to claim 1, wherein the first substance is an aromatic compound.

3. The method according to claim 2, wherein the aromatic compound is diesel.

4. The method according to claim 2, wherein the aromatic compound is—gasoline or lubrication oils.

5. The method according to claim 1, wherein the fluid sample is a refined petroleum product.

6. The method according to claim 1, wherein the material is a first material and wherein the cuvette comprises a second material, different from the first material.

7. The method according to claim 6, wherein the cuvette comprises sidewalls having a first layer defining a cavity and a second layer, wherein the sample fluid is disposed in the cavity, wherein the first layer comprises the first material and the first material comprises cyclic olefin polymer (COP), and wherein the second layer comprises the second material.

8. The method according to claim 7, wherein the first layer is arranged between the cavity and the second layer.

9. The method according to claim 6, wherein the second material is glass or quartz.

10. The method according to claim 1, wherein the threshold rate of change is zero.

11. The method according to claim 6, wherein the first material of the cuvette is COP.

12. The method according to claim 1, wherein the threshold rate of change is greater than zero.

13. The method according to claim 1, further comprising determining a level of a first substance in the fluid sample based on the rate of change in intensity of the light over the duration of time.

14. The method according to claim 13, wherein the rate of change in intensity of the light over the duration of time is proportional to the level of the first substance in the fluid sample.

15. A method for detecting a level of diesel in a fluid sample, the method comprising:

emitting, from a light source of a system, light through a cyclic olefin polymer (COP) cuvette containing the fluid sample, wherein COP of the cuvette is at least partially dissolvable by diesel;

receiving, by a light detector of the system, the light;

measuring an intensity of the received light over a duration of time; and determining, by a computer sub-system of the system, a level of diesel in the fluid sample based on the measured intensity of the received light over the duration of time.

16. The method according to claim 15, wherein determining a level of the diesel in the fluid sample based on the measured intensity over the duration of time comprises:

calculating a rate of change of the intensity of the received light over the duration of time.

17. The method according to claim 15, wherein determining the level of the diesel in the fluid sample based on the measured intensity over the duration of time comprises:

determining a presence of the diesel based on the measured intensity of the received light over the duration of time.

18. The method according to claim 17, wherein determining the presence of the diesel based on the measured intensity of the set of received light over the duration of time comprises:

calculating a measured rate of change of the measured intensity of the received light over the duration of time.

19. The method according to claim 18, wherein a positive measured rate of change indicates the presence of the diesel.

20. The method according to claim 18, wherein a zero or negative measured rate of change indicates the absence of the diesel.

* * * * *